(12) United States Patent
Bobechko et al.

(10) Patent No.: US 6,569,167 B1
(45) Date of Patent: *May 27, 2003

(54) METHOD, APPARATUS AND ASSEMBLY FOR TERMINATING BLEEDING FROM A BONE

(76) Inventors: Walter P. Bobechko, 7777 Forest La., Dallas, TX (US) 75230; Izi Bruker, Linn La., Wayland, MA (US) 01778

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/185,900
(22) Filed: Nov. 4, 1998
(51) Int. Cl.[7] ............................................... A61B 17/56
(52) U.S. Cl. ......................... 606/74; 606/72; 606/232; 128/898
(58) Field of Search ............................. 602/42, 43, 48; 606/72, 74, 232, 61; 623/15.11, 17.11; 128/898; 604/49

(56) References Cited

U.S. PATENT DOCUMENTS

| 5,201,704 A | * | 4/1993 | Ray | 604/49 |
| 5,437,672 A | * | 8/1995 | Alleyne | 606/61 |
| 5,443,483 A | * | 8/1995 | Kirsch | 606/74 |
| 5,569,306 A | * | 10/1996 | Thal | 606/232 |
| 5,653,760 A | * | 8/1997 | Saffran | 606/74 |
| 5,941,901 A | * | 8/1999 | Egan | 606/232 |

* cited by examiner

Primary Examiner—Julian W. Woo
(74) Attorney, Agent, or Firm—Pandiscio & Pandiscio (57) ABSTRACT

A method for terminating bleeding from a portion of a bone, which portion has been opened so as to be subject to bleeding, including the steps of extending a covering over the opened portion of the bone, and fixing the covering to the bone such that the covering is in snug engagement with the opened portion of the bone so as to terminate bleeding from the bone.

12 Claims, 8 Drawing Sheets

METHOD, APPARATUS AND ASSEMBLY FOR TERMINATING BLEEDING FROM A BONE

FIELD OF THE INVENTION

This invention relates to surgical procedures, apparatus and assemblies in general, and more particularly to methods, apparatus and assemblies for terminating bleeding from a bone.

BACKGROUND OF THE INVENTION

In many surgical procedures, a bone must be cut into, or otherwise invaded, or a portion of the bone cut away, or otherwise removed, such that the opened bone bleeds.

In many cases, muscle closely overlies the bone which is to be operated upon. In such a case, this muscle must generally first be separated away from the bone, in order to expose the underlying bone so that it may be operated upon. And in many cases, after the bone has been operated upon, the muscle must be re-positioned back over the bone for proper anatomical restoration.

By way of example, in certain types of spinal surgery, overlying muscle must first be separated away from a selected vertebrae, that vertebrae then cut or otherwise opened so as to accomplish some therapeutic purpose, and then the separated muscle re-positioned back over the vertebrae.

By way of further example, where a bone graft is to be harvested from the iliac crest of the pelvis, overlying muscle must first be separated away from the pelvis, the bone graft removed from the iliac crest, and then the overlying muscle re-positioned back over the pelvis.

In addition to the foregoing, traumatic injury can frequently also cause bleeding from a bone. Depending on the nature of the injury, a surgical procedure may be needed to repair the bone. Again, where muscle closely overlies the bone, the muscle must generally first be separated away from the bone in order to expose the damaged bone for surgical repair and, at the conclusion of the bone repair, the muscle must generally then be re-positioned back over the bone.

Frequently, the opened bone will continue to bleed after the overlying muscle has been re-positioned back over the bone. Depending on the procedure performed, the blood loss from the bone can be substantial, sometimes requiring a blood infusion, with its attendant risks. In addition, the blood exiting the bone often accumulates in the space remaining between the bone and the overlying muscle, thereby causing the formation of a hematoma. The formation of a hematoma can lead to a number of substantial complications. For example, the presence of a hematoma can significantly increase the risk of infection. A drain is often used to help avoid the formation of a hematoma. Unfortunately, however, while the use of such a drain can help reduce the chances of hematoma formation, and hence help reduce the chances of infection, a drain generally does nothing to prevent blood loss.

In other situations, tissue other than muscle may normally closely overlie the bone which is to be operated upon. For example, skin may closely overlie the bone which is to be operated upon. In these situations, the bleeding problems referred to above (i.e., blood loss and hematoma formation) may also exist.

In still other situations, tissue may not normally closely overlie the bone which is to be operated upon. In these situations, hematoma formation may not be significant concern. However, blood loss may still be substantial enough to present a serious problem for the patient.

Thus, there is currently a need for a new procedure, apparatus and assembly for terminating bleeding from a bone, so as to obviate the bleeding problems referred to above.

OBJECTS OF THE INVENTION

Accordingly, one object of the present invention is to provide a method for terminating bleeding from a bone which has been opened so as to be subject to bleeding.

Another object of the present invention is to provide apparatus for terminating bleeding from a bone which has been opened so as to be subject to bleeding.

And another object of the present invention is to provide an assembly for terminating bleeding from a bone which has been opened so as to be subject to bleeding.

A further object of the present invention is to provide a method for forming a bone hemostat for terminating bleeding from a bone which has been opened so as to be subject to bleeding.

And another object of the present invention is to provide a bone hemostat for terminating bleeding from a bone which has been opened so as to be subject to bleeding.

SUMMARY OF THE INVENTION

These and other objects of the present invention are addressed by the provision and use of a novel method for terminating bleeding from a portion of a bone which, in a natural state, has muscle overlying that portion, and which portion has been opened so as to be subject to bleeding, the method comprising the steps of extending the muscle over the opened portion of the bone, and fixing the muscle to the bone such that the muscle is in snug engagement with the opened portion of the bone so as to terminate bleeding therefrom.

The objects of the present invention are also addressed by the provision and use of a novel method for terminating bleeding from a portion of a bone which, in a natural state, has skin overlying that portion, and which portion has been opened so as to be subject to bleeding, the method comprising the steps of extending the skin over the opened portion of the bone, and fixing the skin to the bone such that the skin is in snug engagement with the opened portion of the bone so as to terminate bleeding therefrom.

The objects of the present invention are further addressed by the provision and use of a novel method for terminating bleeding from a portion of a bone which, in a natural state, has a bodily covering overlying that portion, and which portion has been opened so as to be subject to bleeding, the method comprising the steps of extending the bodily covering over the opened portion of the bone, and fixing the bodily covering to the bone such that the bodily covering is in snug engagement with the opened portion of the bone so as to terminate bleeding therefrom, the bone comprising one of a group of bones, the group consisting of a spinal bone and an iliac crest of the pelvis.

The objects of the present invention are further addressed by the provision and use of a novel method for terminating bleeding from a portion of a bone, which portion has been opened so as to be subject to bleeding, the method comprising the steps of extending a bandage over the exposed portion of the bone, and fixing the bandage to the bone such that the bandage is in snug engagement with the opened portion of the bone so as to terminate bleeding therefrom.

The objects of the present invention are still further addressed by the provision and use of novel apparatus for terminating bleeding from a portion of a bone, which portion has been opened so as to be subject to bleeding, the apparatus comprising (1) a covering for disposition over the opened portion of the bone, and (2) a bone anchor for engagement with the bone for holding the covering in snug engagement with the opened portion of the bone so as to terminate bleeding therefrom. In one form of the invention, the covering comprises muscle. In another form of the invention, the covering comprises skin. In another form of the invention, the covering comprises a bodily covering and the bone comprises one of a group of bones, the group consisting of a spinal bone and an iliac crest of the pelvis. And in another form of the invention, the covering comprises a bandage.

The objects of the present invention are still further addressed by the provision and use of a novel assembly for terminating bleeding from a portion of a bone, which portion has been opened so as to be subject to bleeding, the assembly comprising (1) the opened bone, (2) a covering for disposition over the opened portion of the bone, and (3) a bone anchor fixed to the bone and bearing against the covering so as to cause the covering to bear against the opened portion of the bone so as to terminate bleeding therefrom. In one form of the invention, the covering comprises muscle. In another from of the invention, the covering comprises skin. In another form of the invention, the covering comprises a bodily covering and the bone comprises one of a group of bones, the group consisting of a spinal bone and an iliac crest of the pelvis. And in another form of the invention, the covering comprises a bandage.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein.

DETAILED DESCRIPTION Of THE PREFERRED EMBODIMENTS

Figure 1:
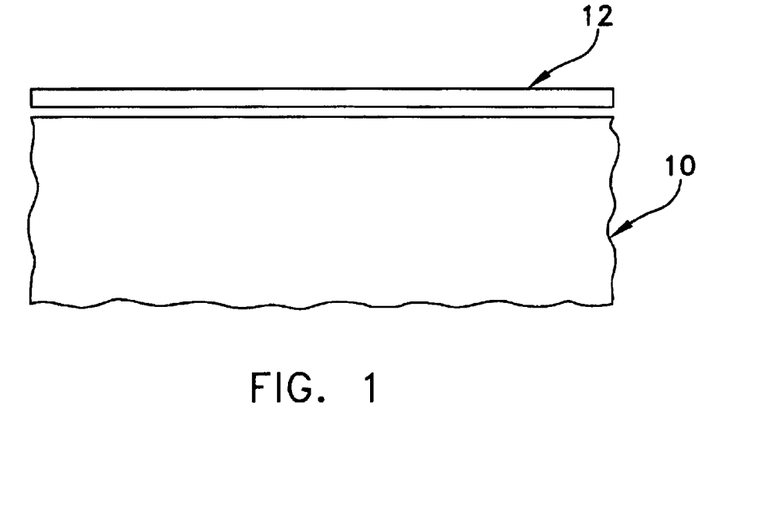
FIG. 1 is a diagrammatic sectional view of a bone, and muscle closely overlying the bone.
Figure 2:
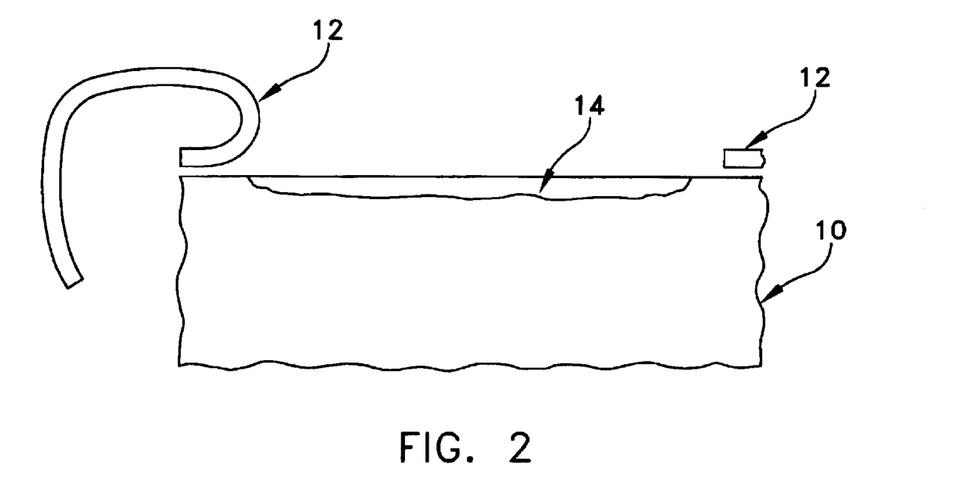
FIG. 2 is a diagrammatic sectional view of the bone and muscle of FIG. 1, with the muscle having been at least partly separated from the bone, and with the bone having been opened so as to be subject to bleeding.

Referring first to FIG. 1, there is shown a bone 10, and a muscle 12 which closely overlies bone 10. In connection with the present invention, in the course of a surgical procedure, muscle 12 is separated at least partly away from bone 10 (e.g., by cutting the muscle) so as to expose the underlying bone, which is then cut, roughened, or otherwise opened so as to produce an opened bone portion 14 which is subject to bleeding (FIG. 2).

Figure 3:
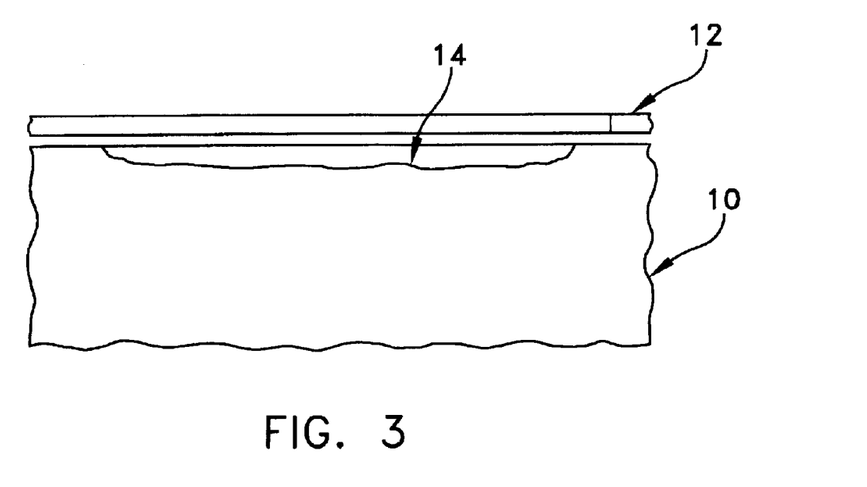
FIG. 3 is similar to FIG. 2, but shows the muscle re-positioned back over the opening formed in the bone.
Figure 4:
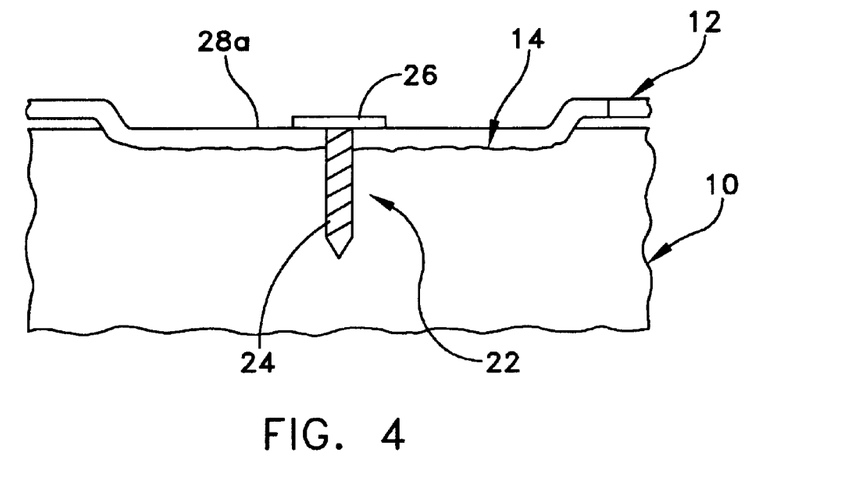
FIG. 4 is similar to FIG. 3, but shows at least one bone anchor extending through the overlying muscle and into the bone so as to terminate bleeding therefrom.

In accordance with the present invention, after bone 10 has been operated upon in the desired manner, muscle 12 is re-positioned back over the bone, so that muscle 12 overlies the opened portion 14 of bone 10 (FIG. 3). Thereafter, at least one nail-type or screw-type bone anchor 22 is driven through muscle 12 and into bone 10 so as to force muscle 12 into snug engagement with the opened portion 14 of bone 10 (FIG. 4). In particular, the bone anchor's shaft 24 is driven through muscle 12 and into bone 10 until the bone anchor's head 26 bears against the upper surface 28a of muscle 12. Bone anchor 22 holds muscle 12 tightly against the bone so as to terminate bleeding from the bone.

If desired, the at least one bone anchor 22 may be driven directly into the bone's open portion 14, in the manner shown in FIG. 4, in which case as few as one bone anchor 22 may be used. Alternatively, the at least one bone anchor 22 may be driven into bone 10 adjacent to the bone's opened portion 14, in the manner shown in FIG. 5, in which case multiple bone anchors will typically (but not necessarily) be used.

By way of example but not limitation, bone anchor 22 may comprise a bone nail or a bone screw of the sort commonly used to attach fracture stabilization hardware to bones.

Figure 5:
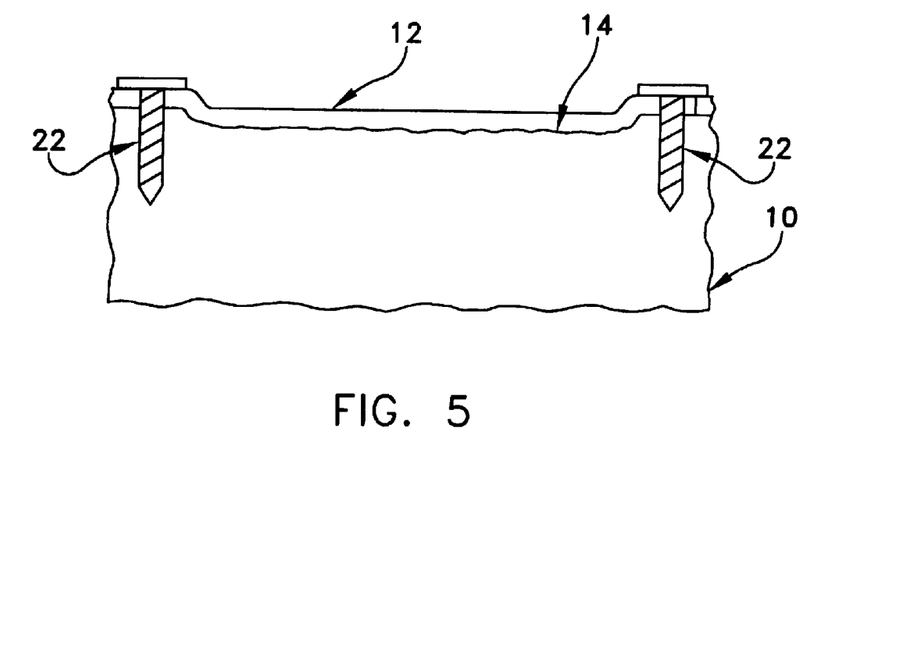
FIG. 5 is similar to FIG. 4, but shows a different manner of deploying the at least one bone anchor through the muscle and into the bone.

If desired, bone anchors other than the nail-type or screw-type bone anchors 22, shown in FIGS. 4 and 5, may be used. In this case, a slightly different procedure may be employed to terminate bleeding from the bone.

Figure 6:
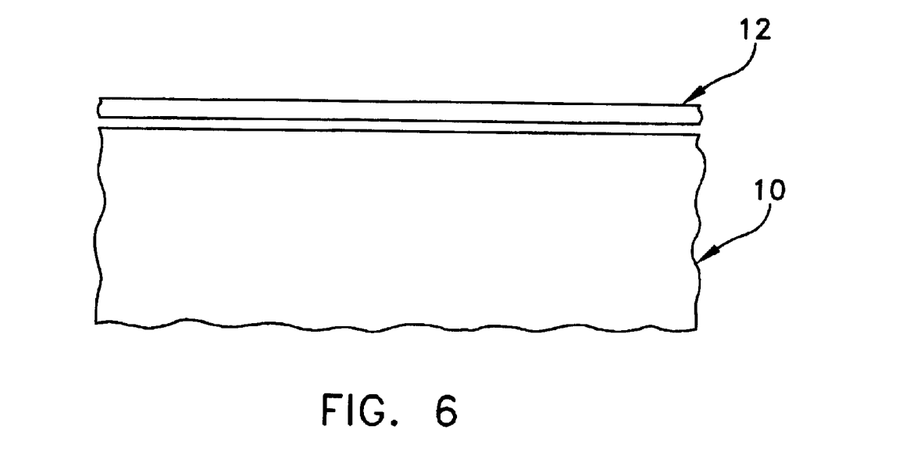
FIG. 6 is similar to FIG. 1.
Figure 7:
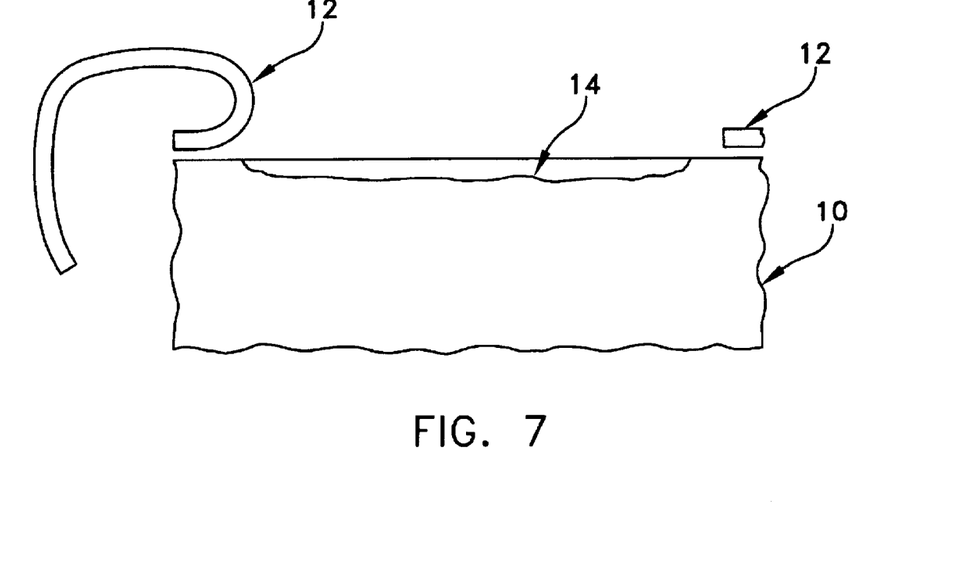
FIG. 7 is similar to FIG. 2.

By way of example but not limitation, a bone anchor comprising suture may also be used. In this case, starting from the condition shown in FIG. 6, muscle 12 is again separated from bone 10 (e.g., by cutting the muscle) so as to expose the underlying bone, which bone is then cut, roughened or otherwise opened so as to produce an opened bone portion 14 which is subject to bleeding (FIG. 7).

Figure 8:
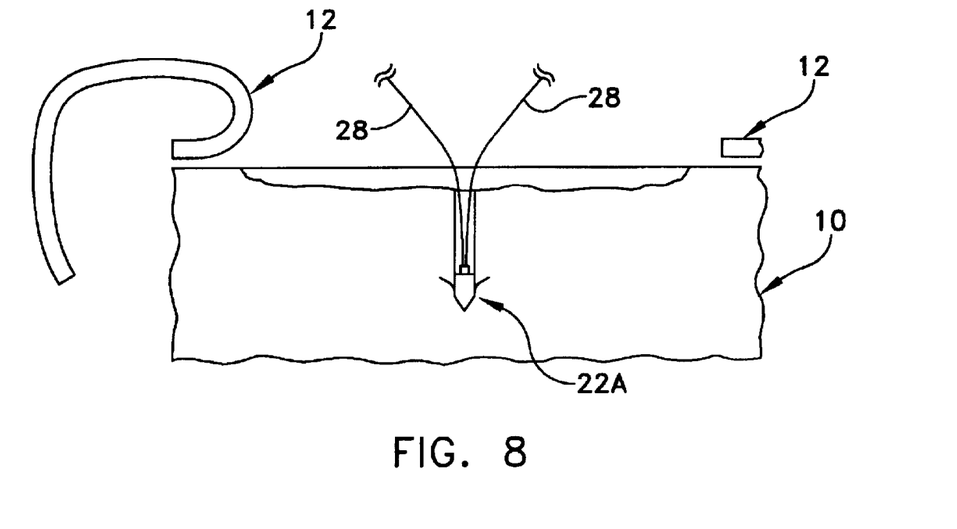
FIG. 8 is similar to FIG. 2, but shows a different type of bone anchor deployed into the bone.
Figure 9:
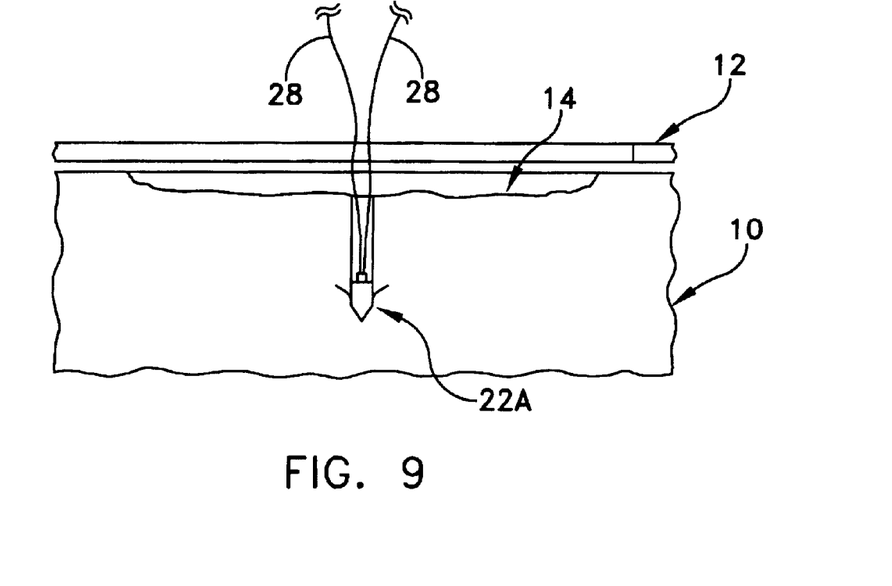
FIG. 9 is similar to FIG. 8, but shows the bone anchor's sutures extending through the muscle, and the muscle re-positioned back over the bone.

In accordance with the present invention, after bone 10 has been operated upon in the desired manner, at least one bone anchor 22A is positioned in the bone, with the bone anchor's sutures 28 extending out of the bone (FIG. 8). Sutures 28 are then passed through muscle 12, and muscle 12 is re-positioned back over the bone, so that muscle 12 once again overlies opened portion 14 of bone 10 (FIG. 9). Sutures 28 are then used to pull muscle 12 into snug engagement with opened portion 14 of bone 10, and a knot 29 is formed in the sutures so as to hold muscle 12 in that position (FIG. 10), whereby to terminate bleeding from the bone.

Figure 10:
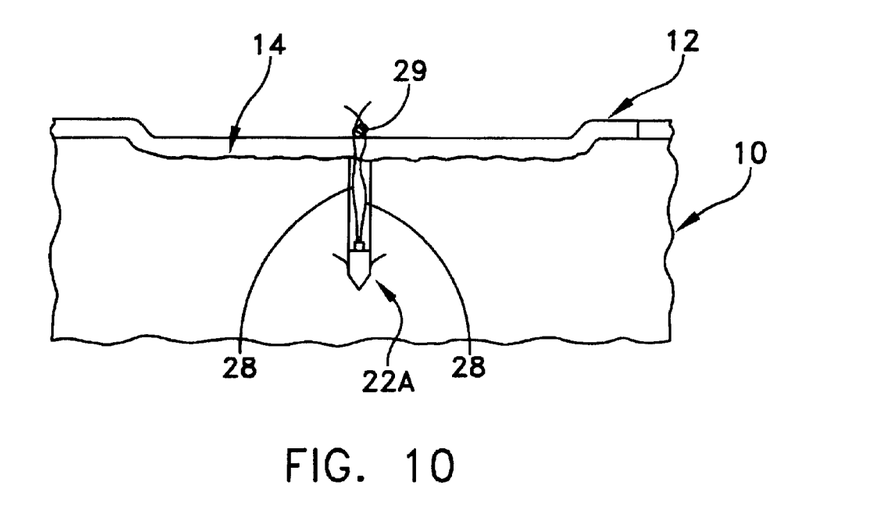
FIG. 10 is similar to FIG. 9, but shows the bone anchor's sutures holding the muscle snugly to the bone so as to terminate bleeding therefrom.

Again, the at least one bone anchor 22A may be deployed directly into the bone's opened portion 14, in the manner shown in FIGS. 8–10. Alternatively, the at least one bone anchor 22A may be deployed into bone 10 adjacent to the bone's opened portion 14, in a manner generally analogous to that shown in FIG. 5, in which case multiple bone anchors will typically (but not necessarily) be used.

By way of example but not limitation, bone anchor 22A may comprise a bone anchor such as that disclosed in U.S. Pat. No. 5,207,679, which bone anchor is illustrated in FIGS. 8–10. Alternatively, bone anchor 22A may comprise a bone anchor such as that disclosed in U.S. Pat. No. 4,632,100, or it may comprise some other type of suture-incorporating bone anchor of the sort well known in the art. The aforementioned U.S. Pat. Nos. 5,207,679 and 4,632,100 are hereby incorporated herein by reference.

It is believed that the foregoing methods, apparatus and assemblies are particularly applicable to surgical procedures involving spinal bones and the iliac crest of the pelvis, where muscle commonly overlies a bone which is to be operated upon. However, the methods, apparatus and assemblies can also be applied with respect to virtually any bone subjected to opening and subsequent bleeding, where muscle commonly overlies the bone which is to be operated upon.

In surgical procedures relative to spinal bones and to the iliac crest of the pelvis, it is contemplated that muscle 12 covering bone 10 will be bisected surgically so as to expose the bone, and that the bone will then be opened surgically. In such procedures, in order to thereafter stop bleeding of the opened bone portion 14, the free edges of the muscle 12 are re-joined and fixed to the bone, preferably by implantation of one or more bone anchors 22 or bone anchors 22A, so as to bring muscle 12 into tight engagement with the opened portion 14 of the bone and hold the muscle in that position, whereby to terminate bone bleeding.

In some circumstances, the bone which is to be operated upon (which may or may not include a spinal bone or an iliac crest of the pelvis) may have bodily tissue other than muscle closely overlying the bone. For example, the bone may have skin closely overlying the bone. In this case, such bodily tissue is snugly attached to the opened portion of the bone in a manner similar to that described above with respect to muscle so as to terminate bleeding from the bone.

Figure 11:
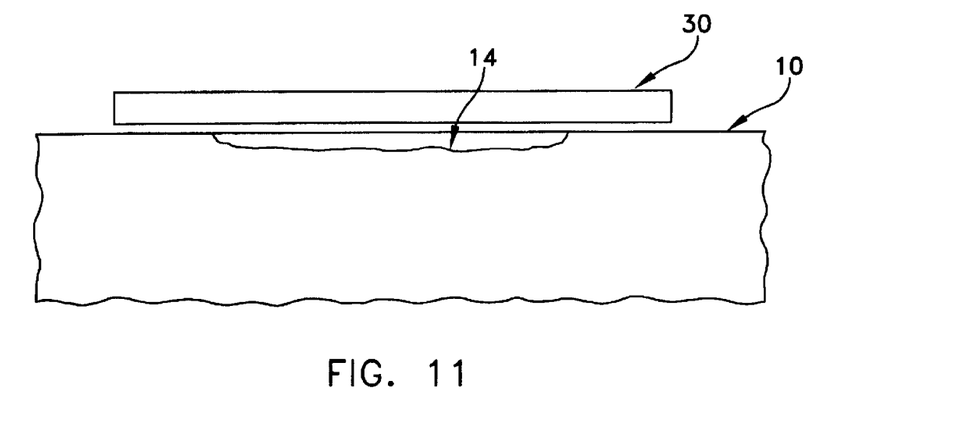
FIGS. 11 and 12 are generally similar to FIGS. 3 and 4, but show the bone anchor holding a bandage snugly against the opened portion of the bone so as to terminate bleeding therefrom.
Figure 12:
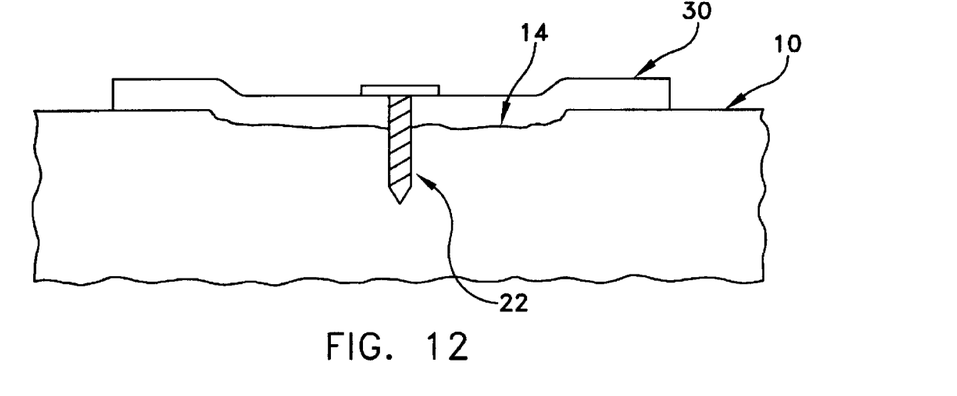

In FIGS. 11 and 12, there is shown an alternative embodiment of the invention which may be used when the bodily tissue normally overlying bone 10 (e.g., muscle 12) is damaged or otherwise not available for covering the opened portion 14 of bone 10, or when bone 10 normally has no closely overlying tissue. In this form of the invention, a bandage 30 is placed against bone 10, overlying the opened portion 14 (FIG. 11). Then at least one bone anchor 22 is driven through bandage 30 and into bone 10 (FIG. 12) so as to force bandage 30 into snug engagement with the opened portion 14 of the bone and hold the bandage in that position so as to terminate bleeding from the bone.

Again, while in FIG. 12 the at least one bone anchor 22 is shown driven into the bone's opened portion 14, the at least one bone anchor 22 could also be deployed into bone 10 about the periphery of opened portion 14, in a manner generally analogous to that shown in FIG. 5.

Figure 13:
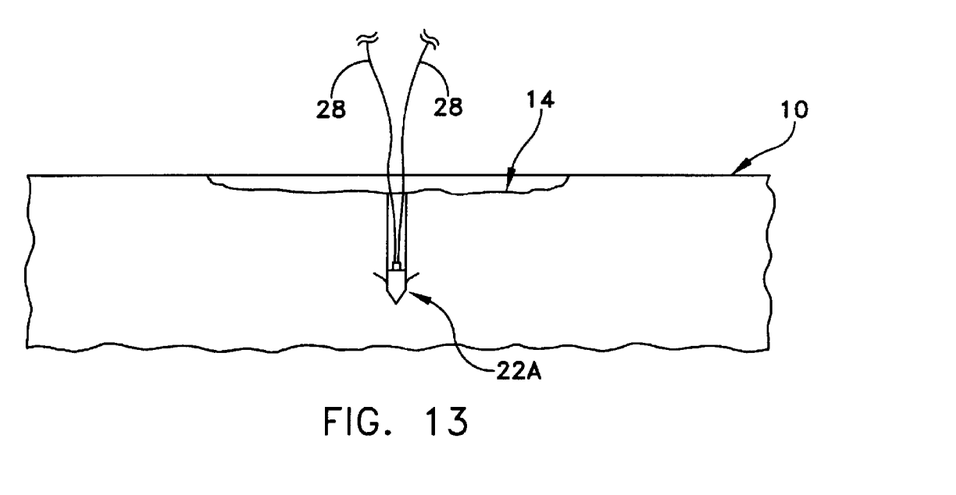
FIGS. 13–15 are generally similar to FIGS. 8–10, but show the bone anchor holding a bandage snugly against the opened portion of the bone so as to terminate bleeding therefrom.
Figure 14:
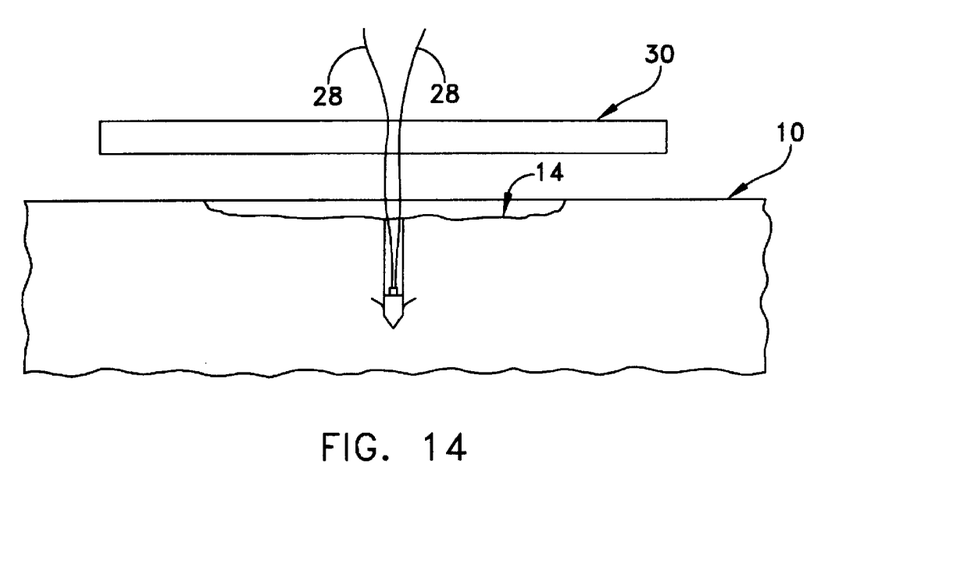
Figure 15:
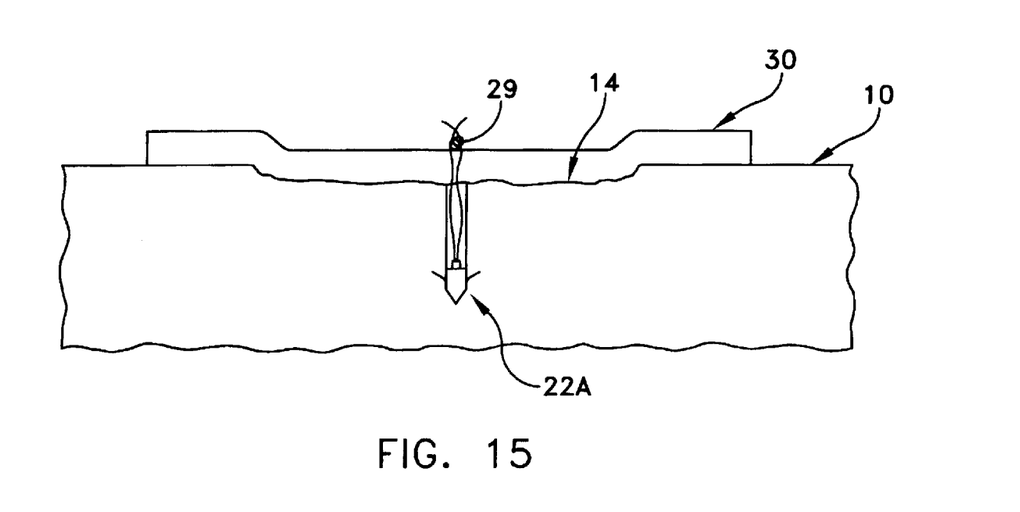

FIGS. 13–15 illustrate how bandage 30 may be attached to bone 10 using at least one bone anchor 22A. In this situation, bone anchor 22A is first set into the bone (FIG. 13). Next, the bone anchor's sutures 28 are passed through bandage 30 and the bandage placed over the bone's open portion (FIG. 14). Then sutures 28 are used to pull bandage 30 into snug engagement with opened portion 14 of bone 10, and a knot 29 formed in the sutures, so as to hold bandage 30 in that position and thereby terminate bleeding from the bone (FIG. 15).

Again, while in FIGS. 13–15 the at least one bone anchor 22A is shown deployed into the bone's opened portion 14, the at least one bone anchor 22A could also be deployed into bone 10 about the periphery of opened portion 14.

Thus, by use of an assembly including only a known covering material, such as muscle or other tissue or a bandage, and a known bone anchor, in combination with the bone itself, bleeding of the bone is stopped or reduced.

It is to be understood that the present invention is by no means limited to the particular constructions herein disclosed and/or shown in the drawings, but also comprises any modifications or equivalents within the scope of the claims.

What is claimed is:

1. A method for terminating bleeding from a portion of a bone which, in a natural state, has muscle overlying that portion, and which portion has been opened so as to expose a substantial portion of the interior of the bone and to be subject to substantial bleeding therefrom, the method comprising the steps of extending the muscle over the opened portion of the bone, and fixing the muscle to the bone using at least one bone anchor, wherein the at least one bone anchor extends into the bone and attaches the muscle in snug engagement with the opened portion of the bone so as to terminate bleeding therefrom.

2. A method according claim 1 wherein the muscle is fixed to the bone by one bone anchor engaged with the bone.

3. A method according to claim 2 wherein the bone anchor is engaged with the bone at the opened portion of the bone.

4. A method according to claim 2 wherein the bone anchor is engaged with the bone about the periphery of the opened portion of the bone.

5. A method according to claim 2 wherein the bone anchor comprises a nail-type bone anchor or a screw-type bone anchor.

6. A method according to claim 2 wherein the bone anchor comprises suture.

7. A method according to claim 1 wherein the bone comprises one of a group of bones, the group consisting of a spinal bone and an iliac crest of the pelvis.

8. A method according to claim 1 wherein the bone comprises a spinal bone, and the muscle has been bisected surgically so as to expose the bone, and the bone has been opened surgically so as to produce the opened portion of the bone.

9. A method according to claim 1 wherein the bone comprises an iliac crest of the pelvis, and the muscle has been bisected surgically so as to expose the bone, and the bone has been opened surgically so as to produce the opened portion of the bone.

10. A method for terminating bleeding from a portion of bone, which portion has been opened so as to be subject to bleeding, the method comprising the steps of extending a bodily covering over the opened portion of the bone, and fixing the bodily covering to the bone using at least one bone anchor, wherein the at least one bone anchor extends into the bone and attaches the bodily covering in snug engagement with the opened portion of the bone, the bodily covering comprising skin.

11. A method for terminating bleeding from a portion of a bone, which portion has been opened so as to expose a substantial portion of the interior of the bone and to be subject to substantial bleeding therefrom, the method comprising the steps of extending a bodily covering over the opened portion of the bone, and fixing the bodily covering to the bone using at least one bone anchor, wherein the at least one bone anchor extends into the bone and attaches the bodily covering in snug engagement with the opened portion of the bone so as to terminate bleeding therefrom, the bone comprising one of a group of bones, the group consisting of a spinal bone and an iliac of the pelvis.

12. A method for terminating bleeding from a portion of a bone, which portion has been opened so as to expose a substantial portion of the interior of the bone and to be subject to substantial bleeding therefrom, the method comprising the steps of extending a bandage over the opened portion of the bone, and fixing the bandage to the bone using at least one bone anchor, wherein the at least one bone anchor extends into the bone and attaches such that the bandage is in snug engagement with the opened portion of the bone so as to terminate the bleeding therefrom.

* * * * *